United States Patent
Merfeld (10) Patent No.: US 7,488,341 B2
(45) Date of Patent: Feb. 10, 2009

(54) METHOD FOR OPTICAL STIMULATION OF THE VESTIBULAR SYSTEM

(75) Inventor: Daniel M. Merfeld, Lincoln, MA (US)

(73) Assignee: Massachusetts Eye & Ear Infirmary, Boston, MA (US)

(*) Notice: Subject to any disclaimer, the term of this patent is extended or adjusted under 35 U.S.C. 154(b) by 443 days.

(21) Appl. No.: 11/227,969

(22) Filed: Sep. 14, 2005

(65) Prior Publication Data

US 2007/0060983 A1   Mar. 15, 2007

(51) Int. Cl.
*A61N 5/06* (2006.01)
(52) U.S. Cl. .............................. 607/88; 607/89; 128/898
(58) Field of Classification Search ............. 607/88–91, 607/92, 42, 93, 94, 118; 128/898
See application file for complete search history.

(56) References Cited

U.S. PATENT DOCUMENTS

| | | | | |
|---|---|---|---|---|
| 4,558,703 A * | 12/1985 | Mark | ............................ | 607/72 |
| 4,592,359 A * | 6/1986 | Galbraith | ...................... | 607/57 |
| 4,754,748 A | 7/1988 | Antowski | | |
| 5,658,322 A | 8/1997 | Fleming | | |
| 5,919,149 A | 7/1999 | Allum | | |
| 5,922,016 A * | 7/1999 | Wagner | ....................... | 607/137 |
| 5,951,596 A * | 9/1999 | Bellinger | ...................... | 607/89 |
| 5,984,859 A * | 11/1999 | Lesinski | ........................ | 600/25 |
| 6,063,046 A | 5/2000 | Allum | | |
| 6,078,838 A | 6/2000 | Rubinstein | | |
| 6,219,578 B1 * | 4/2001 | Collins et al. | ................... | 607/2 |
| 6,219,580 B1 * | 4/2001 | Faltys et al. | .................... | 607/57 |
| 6,295,472 B1 * | 9/2001 | Rubinstein et al. | ............ | 607/55 |
| 6,314,324 B1 * | 11/2001 | Lattner et al. | .................. | 607/42 |
| 6,358,272 B1 | 3/2002 | Wilden | | |
| 6,546,291 B2 * | 4/2003 | Merfeld et al. | ................. | 607/62 |
| 6,735,475 B1 * | 5/2004 | Whitehurst et al. | ........... | 607/46 |
| 6,748,275 B2 | 6/2004 | Lattner et al. | | |
| 6,830,580 B2 * | 12/2004 | Neuberger | ................... | 607/89 |
| 6,921,413 B2 | 7/2005 | Mahadevan-Jansen et al. | ........................... | 607/89 |
| 7,225,028 B2 * | 5/2007 | Della Santina et al. | ......... | 607/57 |
| 2002/0072781 A1 | 6/2002 | Lattner et al. | | |
| 2003/0171787 A1 * | 9/2003 | Money et al. | .................. | 607/57 |
| 2003/0195588 A1 | 10/2003 | Fischell et al. | | |
| 2004/0006287 A1 | 1/2004 | Epley | | |
| 2004/0199223 A1 * | 10/2004 | Andersen et al. | ............... | 607/89 |
| 2004/0215236 A1 | 10/2004 | Lattner et al. | | |
| 2005/0201574 A1 | 9/2005 | Lenhardt | | |
| 2005/0216072 A1 | 9/2005 | Mahadevan-Jansen et al. | ........................... | 607/89 |

(Continued)

FOREIGN PATENT DOCUMENTS

WO   WO 2004045242 A2 *   5/2004

OTHER PUBLICATIONS

U.S. Appl. No. 11/195,568, filed Aug. 1, 2005, Merfeld et al.

(Continued)

*Primary Examiner*—Ahmed M Farah
(74) *Attorney, Agent, or Firm*—Fish & Richardson P.C.

(57) ABSTRACT

An apparatus to stimulate the vestibular system of an individual. The apparatus comprises an optical stimulator configured to optically stimulate a nerve area affecting a person's balance, and a control module coupled to the optical stimulator, the control module being configured to control the optical stimulator.

7 Claims, 5 Drawing Sheets

U.S. PATENT DOCUMENTS

| | | | |
|---|---|---|---|
| 2005/0222644 A1* | 10/2005 | Killian et al. | 607/57 |
| 2005/0267549 A1 | 12/2005 | Della Santina et al. | |
| 2006/0004422 A1* | 1/2006 | De Ridder | 607/45 |
| 2006/0079950 A1* | 4/2006 | Lehnhardt et al. | 607/137 |
| 2006/0161227 A1* | 7/2006 | Walsh et al. | 607/88 |
| 2006/0161255 A1 | 7/2006 | Zarowski et al. | |
| 2007/0012321 A1* | 1/2007 | Zelinsky | 128/898 |
| 2007/0167985 A1* | 7/2007 | Kirby | 607/2 |
| 2008/0172102 A1* | 7/2008 | Shalev | 607/45 |

OTHER PUBLICATIONS

U.S. Appl. No. 11/193,034, filed Jul. 29, 2005, Merfeld et al.

U.S. Appl. No. 11/261,394, filed Oct. 27, 2005, Merfeld et al.

Wells et al. "Optical stimulation of neural tissue in vivo". Optics Letters 30(5):504-506, Mar. 1, 2005.

Gong et al. "Prototype Neural Semicircular Canal Prosthesis Using Patterned Electrical Stimulation". Annals of Biomedical Engineering, vol. 28, pp. 572-581, 2000.

"System Design and Performance of a Unilateral Horizontal Semicircular Canal Prosthesis" by Gong et al., IEEE Transactions on Biomedical Engineering, vol. 49, No. 2, Feb. 2002, pp. 175-181.

Merfeld et al. "Ch. 7.7—*Vestibular Prosthetics*". Neuroprosthetics: Theory and Practice, K. Horch and G. Dhillon, Editors. 2002.

Wall et al. "Vestibular Prostheses: the Engineering & Biomedical Issues". Journal of Vestibular Research 11:1-19, 2002.

Wall et al. "Vestibular Function and Anatomy". Department of Otolaryngology-Head and Neck Surgery, University of Texas Medical Branch, Galveston, TX, pp. 1891-1901, 1998.

\* cited by examiner

METHOD FOR OPTICAL STIMULATION OF THE VESTIBULAR SYSTEM

TECHNICAL FIELD

This invention relates to a medical prosthesis, and more particularly to a vestibular prosthesis.

BACKGROUND

The ability of human beings to maintain stability and balance is controlled by the vestibular system. This system provides the central nervous system with the information needed to maintain balance and stability.

Figure 1:
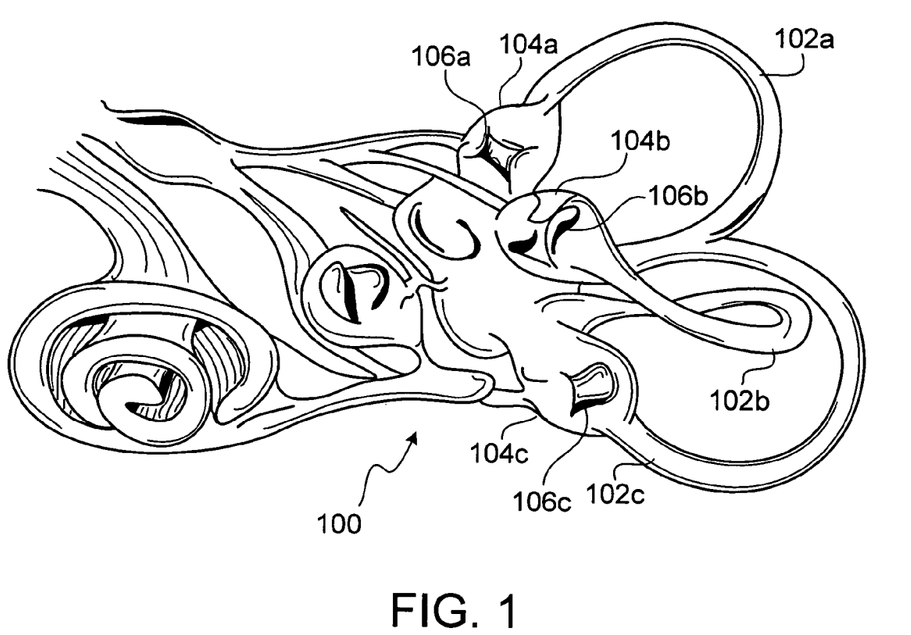
FIG. 1 is a diagram of part of the vestibular system.

FIG. 1 is a diagram showing part of the vestibular system 100. As shown, the vestibular system includes a set of ring-shaped tubes, referred to as the semicircular canals 102a-c, that are filled with the endolymph fluid. The semicircular canals are formed by a membrane called the membranous labyrinth. Each of the semicircular canals 102a-c is disposed inside a hollow bony tube (not shown in the diagram) called the bony labyrinth that extends along the contours of the semicircular canals. As further shown in FIG. 1, each semicircular canal 102a-c terminates in an enlarged balloon-shaped section called the ampulla (marked 104a-c in FIG. 1). Inside each ampulla is the cupula 106a-c, on which hair cells are embedded. Generally, as the semicircular canals 102a-c rotate due to rotational motion of a head, the endolymph fluid inside the canal will lag behind the moving canals, and thus cause the hair cells on the cupula to bend and deform. The deformed hair cells stimulate nerves attached to the hair cells, resulting in the generation of nerve signals that are sent to the central nervous system. These signals are decoded to provide the central nervous system with motion information. The three canals are mutually orthogonal and together provide information about rotation in all three spatial dimensions.

The other endorgans in the vestibular system are the otolith organs, the utricle and the saccule. These endorgans act as linear accelerometers and respond to both linear acceleration and gravity.

In response to the vestibular nerve impulses, the central nervous system experiences motion perception and controls the movement of various muscles thereby enabling the body to maintain its balance.

When some hair cells of peripheral vestibular system are damaged, but others remain viable (as often happens in situations involving bilateral vestibular hypofunction), the central nervous system of a person receives inaccurate information regarding the person's motion. As a result, the person's ability to maintain stability and balance will be compromised. Persons with improperly functioning vestibular systems may consequently experience vertigo, dizziness, and clumsiness, which may lead to collisions and spontaneous falls.

Another type of vestibular system affliction is Meniere's disease. Meniere's disease is a medical condition in which the vestibular system, for unknown reasons, suddenly begins varying the pulse-repetition frequency of the vestibular signal, even when the patient is stationary. This results in severe dizziness. Subsequently, and again for no known reason, the vestibular system begins generating a vestibular signal consistent with the person's spatial orientation, thereby ending the person's symptoms.

One way to remedy symptoms associated with ailments that result in the central nervous system receiving inaccurate motion information is to use prostheses based on electrical stimulation. Such prostheses use implanted or non-implanted transmitting electrodes to cause electrical stimulation of a target nerve (e.g., vestibular nerve ganglion cells). Such electrical stimulation results, for example, in corresponding reflexive responses in the vestibulo-ocular and the vestibulo-spinal pathways, thereby enabling the person to maintain balance and stability in response to the electrical stimulation. Alternatively, such electrodes can target nerves other than those associated with the vestibular system.

Similarly, to alleviate symptoms of Meniere's disease, electrical prostheses can be used to provide a stationary signal to the brain. This can be achieved by producing a jamming signal, through electrical stimulation, that, when combined with a non-stationary signal present on the vestibular nerve, causes the vestibular nerve to provide a stationary signal to the brain. A description of the use of electrical, mechanical, and chemical stimulation of the vestibular system to alleviate Meniere's disease symptoms is provided in U.S. patent application Ser. No. 10/738,920, entitled "Vestibular Stimulator", filed Dec. 16, 2003, the contents of which are hereby incorporated herein by reference in their entirety.

Although useful in providing some relief from vestibular system afflictions, electrical stimulation tends to affect large nerve areas. Such stimulation, therefore, is less useful when refined or focused stimulation is sought. Moreover, electrical stimulation is generally performed using electrodes that have to be positioned proximate to the nerves that those electrode will target. Consequently, when the target nerves are the nerves of the vestibular system, the electrodes have to be surgically implanted close to those nerves. Such a surgical procedure often necessitates cutting through bones surrounding the target nerves, thus resulting in considerable collateral damage to the affected area.

SUMMARY

In one aspect, the invention includes an apparatus to stimulate the vestibular system of an individual. The apparatus comprises an optical stimulator configured to optically stimulate a nerve area affecting a person's balance, and a control module coupled to the optical stimulator, the control module being configured to control the optical stimulator.

In some embodiments the control module is configured to control the optical stimulator by generating a control signal for transmission to the optical stimulator.

In some embodiments, the optical stimulator comprises an optical source configured to generate optical illumination, and an optical fiber coupled to the optical source and disposed proximate to the nerve area. In some embodiments, the optical source includes a laser device.

In some embodiments, the control module controls the optical stimulator in response to motion information indicative of the person's motion. In some embodiments the control module comprises a sensing system that provides the motion information indicative of the person's motion to the control module.

In some embodiments, the control module is configured to provide a jamming signal that causes the optical stimulator to generate optical illumination that stimulates the generation of stationary nerve signals transmitted to the brain. In some embodiments the control module is configured to generate the jamming signal in response to a non-stationary signal detected by a sensor positioned proximate the person's vestibular system.

In some embodiments the apparatus further comprises a power source electrically coupled to the stimulator to power the stimulator.

In another aspect, the invention includes a method for stimulating the vestibular system. The method comprises directing light to stimulate nerve areas affecting a person's balance, and controlling the generation of the light.

The details of one or more embodiments of the invention are set forth in the accompanying drawings and the description below. Other features, objects, and advantages of the invention will be apparent from the description and drawings, and from the claims.

DESCRIPTION OF THE DRAWINGS

Like reference symbols in the various drawings indicate like elements.

DETAILED DESCRIPTION

Figure 2:
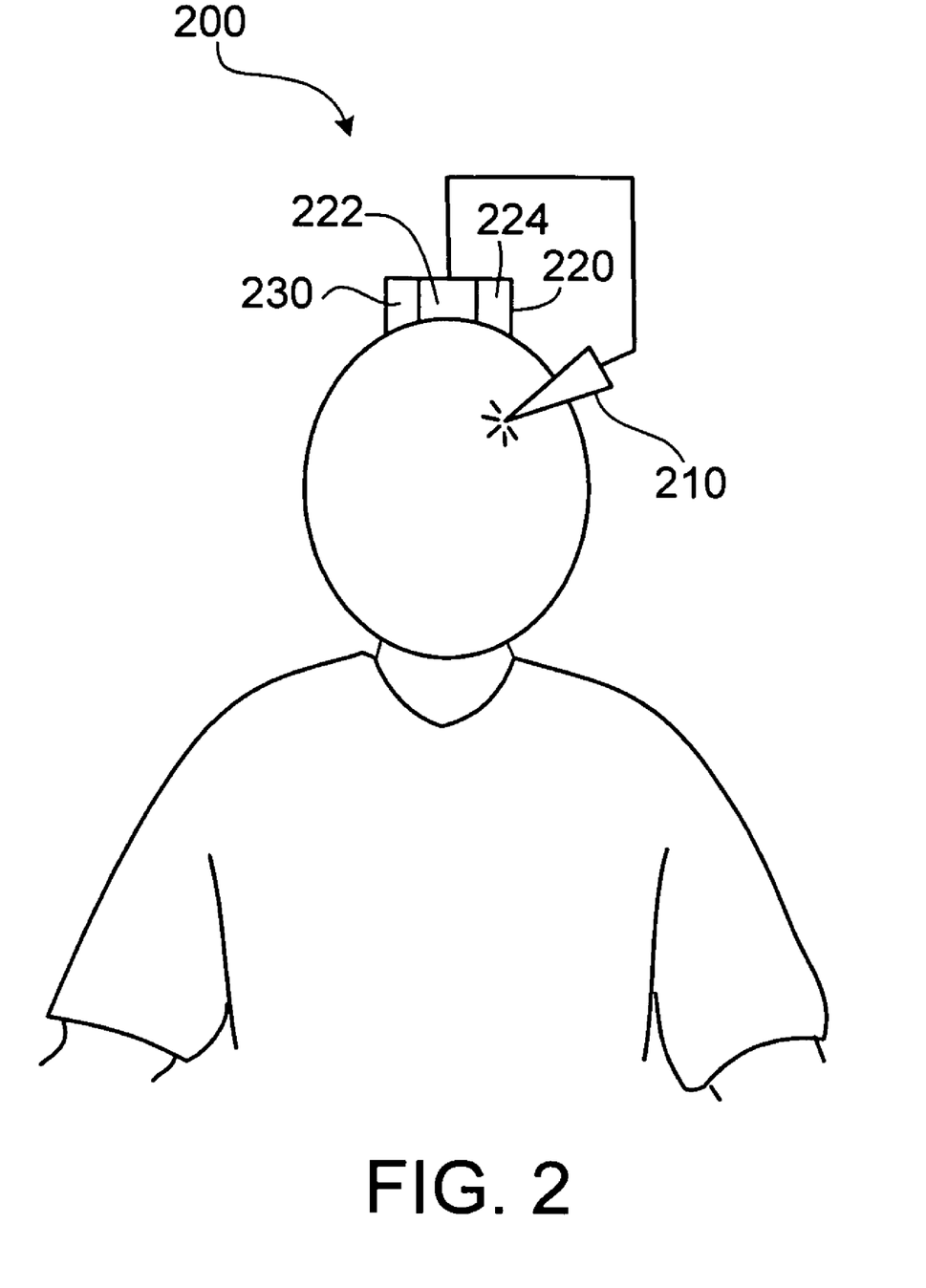
FIG. 2 is a schematic diagram of an embodiment of a vestibular stimulation apparatus.

FIG. 2 is a schematic diagram of a vestibular stimulation apparatus 200 to chronically stimulate a person's vestibular system. The apparatus 200 includes an optical stimulator 210 inserted so that optical illumination from the stimulator 210 can be directed at the vestibular nerves. As will be discussed in greater detail below, the optical stimulator 210 is connected to a control module 220 that controls the optical modulation of the optical stimulator 210, and a power source 230 that powers the optical stimulator 210. The control module includes the sensing system 222, and the computing device 224.

As was reported in the paper "Optical stimulation of neural tissue in vivo" by J. Wells et al. (OPTICS LETTERS/Vol. 30, No. 5/Mar. 1, 2005), neural tissue, including peripheral nerves, may be stimulated using optical radiation. While the exact mechanism that causes neural tissue to be stimulated using optical radiation is not fully understood at this point, it has been hypothesized that optical stimulation causes laser-induced temperature increases. Such transient increases of the tissue temperature possibly trigger the activation of transmembrane ion channels. This activates the neurons by eliciting action potentials, which are the means by which neurons transmit information to the brain.

Figure 3:
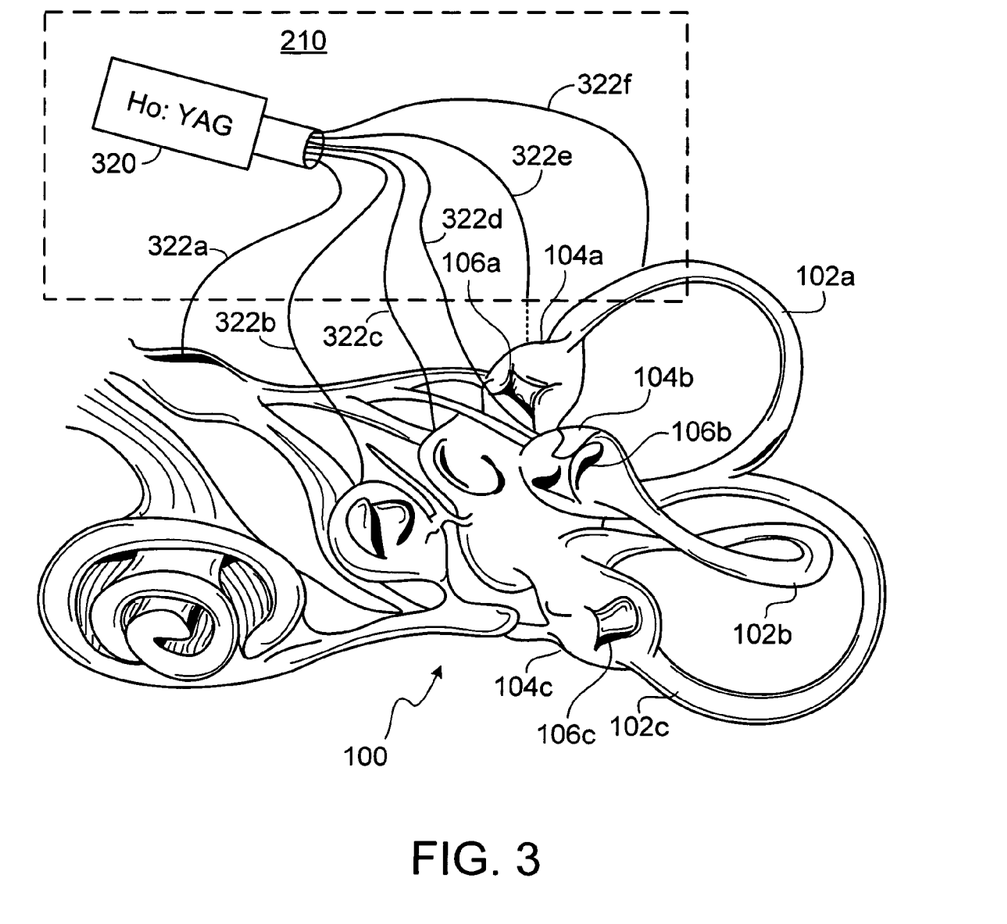
FIG. 3 is a schematic diagram showing the optical stimulator of the apparatus of FIG. 2 disposed about the part of the vestibular system shown in FIG. 1.

FIG. 3 is an exemplary embodiment of the optical stimulator 210 disposed about a portion of vestibular system. The optical stimulator 210 includes an optical source 320 that generates the optical radiation that is used to stimulate the nerves of the vestibular system. The particular optical source 320 shown generates optical radiation in a wavelength range of 2-10 µm. Other optical ranges may also be used. The specific wavelength chosen depends on the type of the nerve tissue that is to be stimulated. The wavelength chosen must be one that can cause stimulation of the nerve tissue without damaging that nerve tissue. A useful indicator of suitable wavelengths for achieving damage-free stimulation is the safety-ratio, defined as the ratio of the ablation threshold of radiant exposure and the exposure power needed to stimulate the nerve. The ablation threshold is defined as the point at which the absorbed optical energy is sufficient to break the bonds between molecules of the material absorbing it. Thus, high safety ratios are indicative of suitable optical wavelength. Empirical data suggests that suitable optical wavelengths to stimulate the nerves of the vestibular system are 2.1 µm and 4 µm.

An optical source that generates optical radiation having a wavelength of 2.1 µm is a holmium:YAG laser. At that wavelength, the average stimulation threshold for neural nerves is 0.32 J/cm$^2$, whereas the associated ablation threshold is 2.0 J/cm$^2$. Thus, at a wavelength of 2.1 µm, the safety ratio is approximately 6.25, which enables efficient stimulation of the neural nerves using laser illumination without damaging them. Other lasers generating optical radiation at that wavelength, or other suitable wavelengths may also be used. For example, white-light generators fitted with variable-length optical filters may be used to generate optical radiation of particular wavelengths.

The optical source 320 may be placed outside the body, preferably at some inconspicuous and unobtrusive location around the head of the individual wearer, for example, behind the individual's ear. Alternatively, the optical source 320 may be placed at other locations on the body. Preferably, however, the optical source should be placed to avoid propagating optical radiation for distances that result in significant optical power attenuation en route to the vestibular system. The optical source 320 may, in some embodiments, comprise several independent optical sources, such as separate laser sources, each independently provides optical stimulation to separate nerve areas of the vestibular system.

In some embodiments, the optical source 320 is internally placed proximate the vestibular system. For example, laser diodes, and other photon generating devices that are small enough to be implanted in the interior of the head proximate to the vestibular system, may be used.

Because optical radiation is highly focused, the optical illumination that irradiates a vestibular nerve will generally affect a relatively small localized area of that vestibular nerve. Accordingly, to efficiently stimulate the vestibular system, it is necessary to separately irradiate several nerve areas in the vestibular system. As shown in FIG. 3, to stimulate a plurality of nerve areas affecting the central nervous system's ability to maintain a person's balance, the optical radiation generated by the optical source 320 is directed via optical fibers 322a-f to various locations in the part of the vestibular system shown in FIG. 3. Although six optical fibers are shown in the figure, additional optical fibers may be used.

For example, optical fiber 322d is shown disposed proximate the cupula 106b in the ampulla 104b, and is thus configured to illuminate, and thereby stimulate, the nerve endings in the cupula 106b. Other optical fibers are disposed proximate to other areas in the vestibular system in which vestibular nerve endings are bundled. The illuminated nerve areas include not only the nerves connected to the hair cells in the various cupulas of the vestibular system 100, but also nerve areas at the vestibular system's other sensing organs, such as the otolith organs. Further, optical fibers may be disposed in other areas of the body to directly illuminate nerves connected to the motion processing part of the central nervous system, like the vestibular nuclei or vestibulo-cerebellum.

Alternatively, rather than having fiber optics transmit optical radiation generated by an optical source 320, individual implanted optical sources, such as laser diodes may be directly disposed in and around the nerve areas of the vestibular system 100.

In FIG. 3, the optical fibers extend subcutaneously from an interface coupling the optical source 320 to the optical fibers, to their various locations in and around the vestibular system.

Accordingly, the optical fibers 322a-f are constructed from bio-compatible materials. For example, bio-compatible glass materials may be used to construct optical fibers. Alternatively, fibers 322a-f can be coated with layers of bio-compatible materials like Teflon or silicone. Other suitable bio-compatible materials include metallic materials such as stainless steel or titanium, or various types of ceramics that are approved for medical applications. As a further alternative, the optical fibers 322a-f may extend within subcutaneous catheters that shield the optical fibers 322a-f from body fluids and tissues.

The use of optical fibers reduces the infliction of body trauma during surgical insertion. Because optical stimulation tends to be more focused than, for example, electrical stimulation, and can also propagate through translucent media (i.e., media that are partially, but not completely opaque), optical fibers may, in some circumstances, be placed opposite vestibular nerve areas surrounded by a translucent or semi-opaque barriers without having to breach that barrier. For example, nerves emerging from the bony shell en route to the brainstem may be directly illuminated with optical illumination without having to breach any bony barrier. Further, even where vestibular nerves are surrounded by a bone, such as the bony labyrinth, optical radiation can propagate through the bony tissue and reach the nerves if the bone is sufficiently thin. Thus, in some locations in the vestibular systems, placement of the fiber optics near vestibular nerves surrounded by a bone would, at most, require that the bone be thinned. There would be no need to actually cut or otherwise breach the bone. Accordingly, the use of optical stimulation can reduce the risk of damage to the vestibular system.

The optical fibers 322a-f thus carry optical illumination from an optical source 320. The level of optical illumination transmitted from the optical source 320 through each of the optical fibers 322a-f (i.e., the illumination power amplitude), as well as the illumination duration and/or frequency, is determined according to the control mechanism 220 (in FIG. 2) that modulates the generation of optical illumination by the optical source 320. Control signals generated by the control module 220 are transmitted to the optical stimulator 210.

Specifically, if the optical stimulator 210 is to be used to convey motion information to the vestibular system, the amplitude, frequency and/or duration of optical illumination transmitted through each optical fiber and projected onto the target nerve areas will depend on the linear and rotational displacement of the person's head. Thus, for example, if a person's head experiences a particular angular acceleration over a particular time, the amplitude level, frequency and/or duration of the optical illumination transmitted through those optical fibers disposed proximate to the corresponding cupulas will be commensurate with the rotation of the head.

On the other hand, if the optical stimulator 210 is to be used to counteract the symptoms of Meniere's disease, the amplitude level, frequency, and/or duration of the optical illumination will be such that resultant stimulated stationary nerve signals will be delivered to the central nervous system.

The control module 220 includes a motion sensing system 222 that determines the person's movement, including rotation, translation, and/or orientation with respect to gravity. Data regarding a person's motion is used to modulate the optical stimulation that provides the central nervous system with motion information. Examples of a motion sensing system are provided in U.S. Pat. No. 6,546,291, entitled "Balance Prosthesis," the contents of which are hereby incorporated by reference in their entirety.

Figure 4:
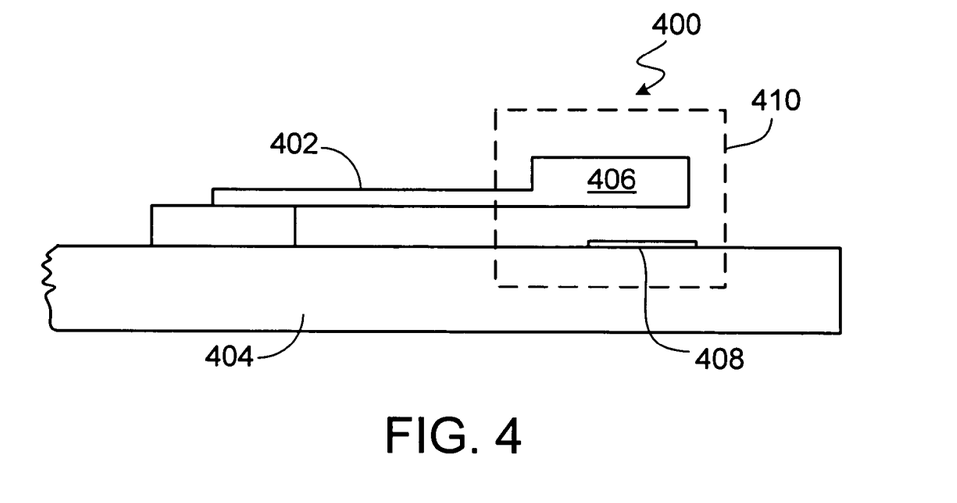
FIG. 4 is a translation sensor for use with the apparatus of FIG. 2.

Generally, the motion sensing system 222 used to determine motion information for individuals having a damaged vestibular system includes translation sensors and rotational sensors. These sensors typically include three translation sensors configured to sense the person's translation along the three coordinate axes and/or three rotation sensors configured to sense rotations along the three axes. An exemplary translation sensing device 400 is shown in FIG. 4. As shown, the translation sensing device 400 is a micro-mechanical device on which a cantilevered beam 402 is mounted on a substrate 404. The beam 402 suspends a proof mass 406 above a sense electrode 408. The proof mass 406 and the sense electrode 408 together form a capacitor 410 having a capacitance that depends in part on the gap separating the proof mass 406 from the sense electrode 408. An acceleration normal to the substrate 404 results in a force that deflects the proof mass 406 toward or away from the sense electrode 408, thereby changing the capacitance. This change in capacitance modulates a signal, which thus carries information indicative of acceleration normal to the cantilevered beam 402.

Figure 5:
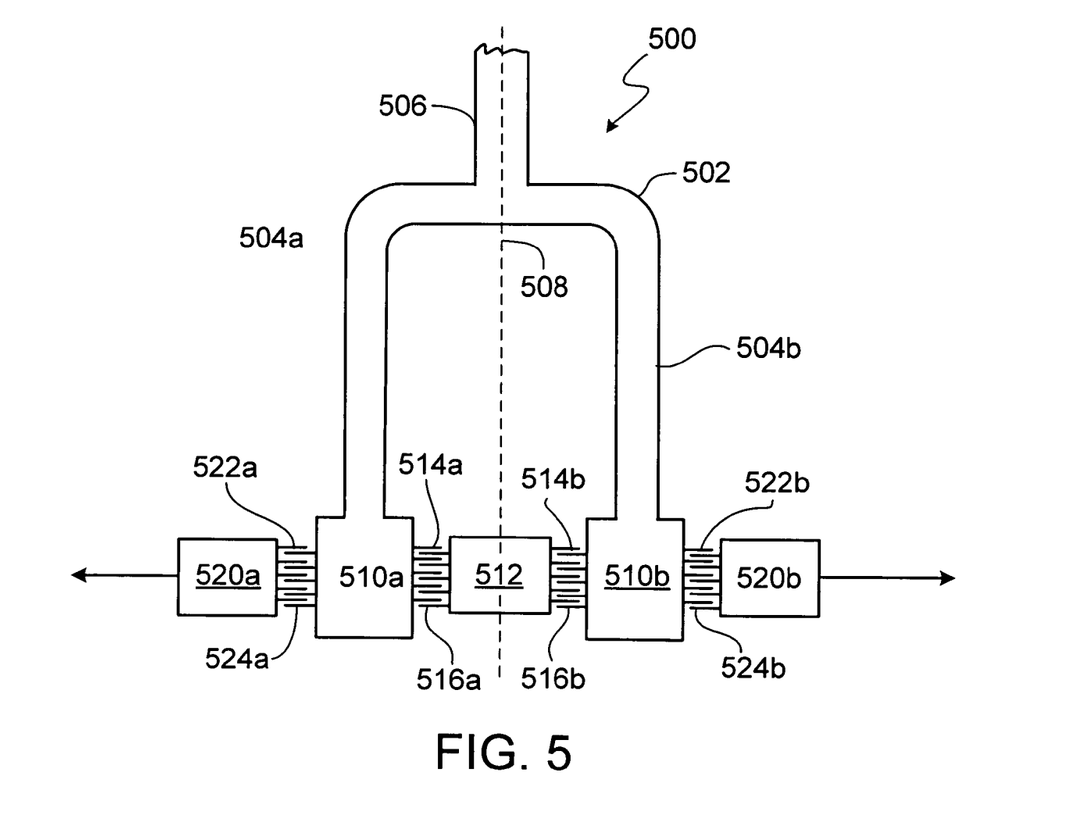
FIG. 5 is a plan view of a rotation sensor for use with the apparatus of FIG. 2.

FIG. 5 is an exemplary rotation sensing device 500. As shown, the rotation sensing device 500 is a micro-mechanical device that includes a tuning fork 502 having first and second parallel tines 504a, 504b connected to a base 506. A line extending through the base 506 and parallel to the first and second tines 504a, 504b defines a central axis 508 of the tuning fork 502. The first and second tines 504a, 504b of the tuning fork 502, when the tuning fork 502 is in its equilibrium position, define an equilibrium plane. First and second proof masses 510a, 510b are integrated onto the ends of the first and second tines 504a, 504b respectively.

The rotation sensor 500 also includes an inner comb 512 disposed between the first and second proof masses 510a, 510b. The inner comb has two sets of teeth 514a, 514b, each of which extends away from the central axis 508 in the equilibrium plane. Each proof mass 510a, 510b includes a plurality of inner teeth 516a, 516b extending toward the central axis in the equilibrium plane. These inner teeth 516a, 516b interdigitate with the corresponding teeth 514a, 514b extending from the inner comb 512.

The rotation sensor 500 also includes two outer combs 520a, 520b, each disposed adjacent to a proof mass 510a, 510b. Each outer comb 520a, 520b has a plurality of teeth 522a, 522b extending inwardly toward the central axis 508 in the equilibrium plane. Each proof mass 510a, 510b includes a plurality of outer teeth 524a, 524b that extend away from the central axis 508 in the equilibrium plane. These outer teeth 524a, 524b interdigitate with the corresponding teeth 522a, 522b on the outer combs 520a, 520b.

Figure 6:
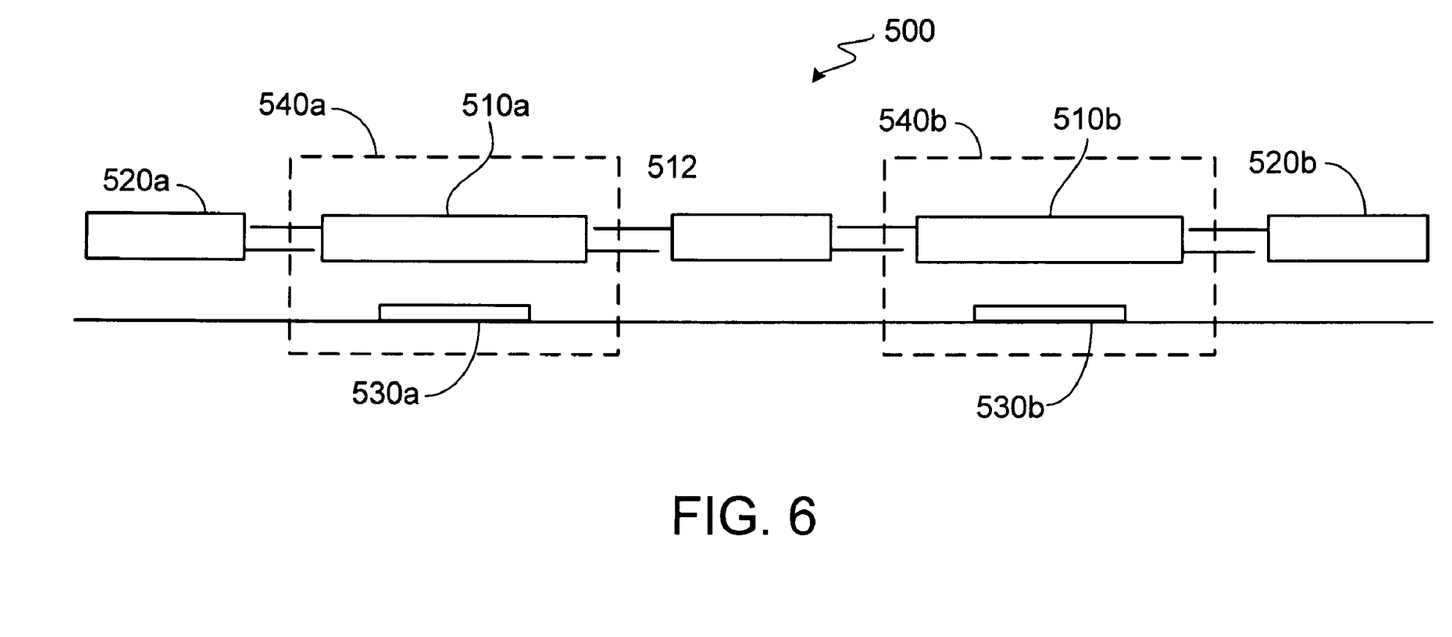
FIG. 6 is a cross-sectional view of the rotation sensor of FIG. 5.

The proof masses 510a, 510b are suspended above first and second sense electrodes 530a, 530b, as shown in the cross-section of FIG. 6. Each proof mass 510a, 510b and its corresponding sense electrode 530a, 530b thus defines a capacitor 540a, 540b having a capacitance that depends on the position of the proof mass 510a, 510b relative to the sense electrode 530a, 530b.

The inner and outer combs 512, 520a, 520b are connected to a voltage source that generates a voltage on their respective teeth 514a, 514b, 522a, 522b. This results in the generation of an electrostatic force that deflects the proof masses 510a, 510b in the equilibrium plane. The voltage on the teeth 514a, 514b, 522a, 522b of the inner and outer combs 512, 520a, 520b is selected to cause oscillation of the proof masses 510a, 510b in the equilibrium plane. To maintain oscillation, the rotation sensor consumes approximately 0.2 watts from a 5 volt DC source. The oscillation of the proof masses 510a, 510b results in the generation of an equilibrium angular momentum vector that is perpendicular to the equilibrium plane and an equilibrium capacitance signal measured at the sense electrodes 530a, 530b.

When the person wearing the rotation sensor 500 experiences a rotation, the angular momentum vector points in a different direction relative to a fixed reference frame associated with the wearer's surroundings. Because angular momentum of the oscillating proof masses 510a, 510b is conserved, a torque is generated that causes the proof masses 510a, 510b to oscillate above and below the equilibrium plane. This causes the angular momentum vector to recover its original direction.

As the proof masses 510a, 510b oscillate above and below the equilibrium plane, the capacitance of the capacitors 540a, 540b changes. This change provides a signal indicative of rotational motion experienced by the rotation sensor 500. The dynamic response of the rotation sensor 500 has a bandwidth between 100 and 1000 Hz and a maximum rate range of 400 degrees per second.

It will be understood that other types of translation and rotation sensors having different configurations and designs may be used instead of the translation and/or rotation sensors shown in FIG. 4 and FIGS. 5-6 respectively.

Returning to FIG. 2, the motion sensing system 222, which includes one or more sensing instruments such as a translation sensing device 400 and/or rotation sensing device 500, is secured to the person's head, thereby enabling the sensing device to sense motion of the person's head. The relatively small size of the sensing system 222 enables placement of the sensing system 222 on the external surface of the head, preferably at an inconspicuous and unobtrusive location. Alternatively, the sensing system 222 may be placed underneath the surface of the head, or at other locations on the person's body.

The control module 220 also includes a computing device 224, which can perform computations using digital and/or analog techniques. One of the functions the computing device 224 is configured to perform is to receive data from the various sensing devices of the motion sensing system 222, to process the data, and to generate output control information to be sent to the optical stimulator 210. Some operations that computing device 224 thus performs include filtering and scaling of the input motion data.

For example, sample streams from the rotation sensing devices employed by the motion sensing system 222 may be passed through integrators to obtain angular displacements. The outputs of the integrators can then be passed through high-pass filters to remove low-frequency errors introduced by variations in the rotation sensors' bias voltages. Another processing operation that can be performed by the computing device 224 includes passing motion data from the translation sensing devices employed by motion sensing system 222 through low-pass filters to remove high-frequency contributions from the rotation sensing devices. Suitable low-pass filters include third-order Butterworth filters having minus 3 dB points near, for example, 0.03 Hz. The outputs of the high-pass filters that processed the rotational motion data and the low-pass filters that processed the translation motion data can then be passed through corresponding summers to obtain an estimate of the wearer's orientation in an inertial coordinate system.

Other types of processing that the computing device 224 may be configured to perform can also include the implementation of a procedure to resolve the translation motion data into its various components to distinguish between acceleration that results in translation and acceleration caused by gravity. In particular, by using a pre-determined initial gravity vector g(0), and using the rotation data obtained from the rotation sensing devices, a rotation transformation can be performed to estimate the magnitude and direction of a gravity vector g(t) at any instant. This gravity vector can then be subtracted from the translation motion data to derive the three linear translation motion vectors at that instant due to linear acceleration corresponding to the actual translation of the wearer.

Another type of processing that may be performed by the computing device 224 includes the determination of the person's orientation in an inertial coordinate system. For example, a Kalman filter that incorporates a model of the dynamic characteristics of the motion sensing system 222 and of the person can be used to derive such an estimate. The resulting estimates from the computing device 224 can be provided to an encoder for translation into a control signal that can be used to control the optical stimulator 210 and thereby stimulate the person's vestibular system.

The control module 220 is also configured to provide a jamming signal when the stimulator apparatus is to be used for the purpose of alleviating Meniere's diseases symptoms. In this case, the computing device 224 is configured to generate a jamming signal that is used to cause the optical source 320 to generate a properly modulated optical signal to stimulate the vestibular system to counteract the symptoms of Meniere's disease.

The jamming signal characteristics are selected such that the resulting jamming signal causes the vestibular system to generate a constant-repetition signal which in effect drowns out the time-varying signals produced by the malfunctioning vestibular system of the patient suffering from Meniere's disease. One type of signal that can be generated by the computing device 224 to modulate the generation of optical illumination by optical source 320 is a pulse train having a controllable pulse amplitude and a pulse repetition frequency. The signal generated by computing device 224 thus causes the nerves of the vestibular system to generate a nerve signal having a constant pulse-repetition frequency. A time-varying signal of this type, the spectrum of which is substantially constant in time, is often referred to as a "stationary signal." In one embodiment, the pulse-repetition frequency is approximately equal to the maximum neuron firing rate, which is typically on the order of 450 Hz. This pulse-repetition frequency is likely to result in the synchronous firing of neurons at or near their maximum firing rate. However, it may be useful in some cases to have a much higher pulse-repetition frequency, for example in the 1-10 kilohertz range, so that neurons fire asynchronously.

The jamming signal generated by the computing device 224 may cause the optical source 320 of the optical stimulator 210 to produce other type of time-varying jamming signals to stimulate the vestibular system nerves. Examples of other jamming signals include sinusoidal signals or other oscillatory signals.

The jamming signal need only be on during an attack of Meniere's disease. When the attack subsides, the jamming signal is removed and the patient regains normal vestibular function. The computing device 224 thus includes a mechanism for applying and suspending the generation of the jamming signal.

For example, the computing device 224 has a patient-accessible switch located on a user interface (not shown) connected to the control module 220. When the patient feels the onset of a Meniere's disease attack, he uses the switch to apply the jamming signal. A disadvantage of this type of control unit is that because the jamming signal masks the symptoms of the attack, the patient is unable to tell whether the attack is over. Alternatively, the patient can simply use the switch to turn off the jamming signal after a reasonable time has elapsed. The resulting change in the pulse-repetition frequency of the signal received by the brain may result in some dizziness. However, if the attack of Meniere's disease is in fact over, this dizziness should abate shortly. If the dizziness does not abate, the patient uses the switch to turn the jamming signal on again.

Alternatively, the signal suspension mechanism of the computing device 224 can include a timer that automatically turns the jamming signal off after the lapse of a pre-determined jamming interval. In some embodiments, the length of the jamming interval is user-controlled and can be entered through the user interface, whereas in others, the length of the jamming interval is hard-wired into the control unit. If the dizziness does not fade after the jamming signal has been turned off, the patient uses the switch on the user interface to turn the jamming signal on again.

In some embodiments, the computing device 224 includes an automatic control unit having one or more sensors (not shown) that are implanted proximate to the vestibular system to measure the vestibular signal. When the control unit detects time-varying changes in the pulse-repetition frequency of the vestibular signal indicative of the onset of an episode of Meniere's disease, it causes the computing device 224 to generate the jamming control signal that is transmitted to the optical stimulator 210 to modulate the generation of optical illumination. In this case, the jamming signal characteristics can be made to vary in response to the characteristics of the measured vestibular signal.

The resultant control signals sent to the optical stimulator 210 can be provided continuously. For example, when signals corresponding to a person's motion are transmitted to stimulator 210, the control signal continuously transmits information regarding the characteristics of the optical illumination to be generated. Alternatively, the control signals sent to the optical stimulator 210 can be sent as short bursts separated by pre-determined intervals (e.g., every 10 ms). Control signals sent as short bursts can carry information regarding the level, duration and/or frequency of the optical illumination. For example, based on a signal level provided by the sensing device of the motion sensing system 222, the computing device 224 can determine a corresponding control feedback signal representing a discrete amplitude value, frequency value, and/or time duration to be sent to the optical stimulator 210 to cause the central nervous system to properly stabilize and balance the person's body and/or head.

When the computing device 224 generates a constant jamming signal to counteract the symptoms of Meniere's disease, the computing device 224 can transmit a one-time signal that causes the optical source 320 of the optical stimulator 210 to generate optical illumination at a constant repetition rate, thereby stimulating the vestibular nerves to produce nerve signals at a constant rate. When the symptoms of Meniere's disease subside, the computing device 224 can generate a signal that causes the optical stimulator to suspend the generation of optical illumination.

Since the optical stimulator 210 includes one or more optical fibers connected to the optical source 320, each of the optical fibers is controlled individually. This can be achieved by having the computing device 224 generate control signals that separately control the optical illumination transmitted through each of the optical fibers 322a-f. Alternatively, in embodiments having multiple optical sources, the computing device generates control signals that control each of the optical sources of the optical stimulator 210.

If a single optical source 320 is used to generate optical illumination at the various optical fibers, the control signals can be sent using time-division multiplexing. In this case, control signals to control the generation of optical illumination at each optical fiber 322a-f are sent in sequence. Other methods for transmitting control signals from computing device 224 to the optical stimulator 210 can also be used. The optical source 320 can use the control signals it receives from the computing device 224 to sequentially generate the optical illumination to be transmitted through each of the optical fibers 322a-f using a similar time-division multiplexing scheme. Using such a scheme thus enables the optical stimulator 210 to independently control and generate the optical stimulation at various nerve areas so that different nerve areas are exposed to different optical stimulation. Alternatively, the optical source 320 can simultaneously generate the optical illumination transmitted through the optical fibers using, for example, a wavelength division multiplexing scheme. Implementation of a wavelength division multiplexing would require that the optical source be capable of generating optical illumination at different wavelengths. Such a scheme would enable simultaneous independent control of the various optical fibers 322a-f. Alternatively, in some embodiments the optical source 320 may provide the same level of optical illumination to each of the optical fibers. Such embodiments may be particularly useful when the apparatus 200 is used to counteract Meniere's disease symptom by causing the vestibular nerves to generate nerve signal at a constant repetition rate, thereby effectively drowning out the non-stationary signal produced by the patient's malfunctioning vestibular system.

The computing device 224 may include a computer and/or other types of processor-based devices suitable for multiple applications. Such devices can include volatile and non-volatile memory elements, and peripheral devices to enable input/output functionality. Such peripheral devices include, for example, a CD-ROM drive and/or floppy drive, or a network connection, for downloading software containing computer instructions to enable general operation of the processor-based device, and for downloading software implementation programs to process input motion data and generate corresponding control information to control the generation of optical illumination by an optical source, and/or to generate control signals to control the generation of optical illumination jamming signals. Additionally or alternatively, the computing device 224 may include a digital signal processor (DSP) to perform the various processing functions described above. A suitable DSP is the Analog Devices ADSP 2183 processor.

The computing device 224 is placed on the person's head proximate to the sensing system 222, thereby minimizing the distance that signals from the sensing devices have to travel to reach the computing device. However, the location of the computing device 224 is not critical. The device 224 can thus be placed anywhere on or off the person's body.

As noted above, the control device 220 also includes a user interface (not shown) to enable direct control by a user (such as the person wearing the optical stimulator, a physician, or a technician) to control the generation of optical illumination by the optical source 320 of the stimulator 210. Input entered through the user interface is processed by the computing device 224 to generate corresponding control signals for the stimulator 210. Typical user interfaces include a small key pad to enable the user to enter data, and/or a switch for activating or suspending the generation of a jamming signal. Such a key pad, and/or switch, could be attached to a housing in which the computing device 224 is held. However, the user interface need not be located proximate to the computing device 224. For example, a computer console can be remotely linked to the computing device 224, either using wireless transmission, or by direct physical coupling. Executing on such a computer console would be, for example, a graphical user interface to enable the user to enter the data for controlling the optical stimulator 210.

FIG. 2 further shows that the optical stimulator also includes a power source 230 to power, among other things, the sensing system 222 and/or the stimulator 210. The power source 230 may be a battery carried or attached to the person. The power source 230 is electrically coupled to the control module 220 and/or the optical stimulator 210 using electrical conducting wires. Alternatively, powering of the control module 220 and the stimulator 210 may be implemented through power telemetry, in which power is delivered to the stimulator 210 and/or the control module 220 via wireless power transmission. In some embodiments the power source 230 may include several independent power units. For example, a battery for delivering sufficient power to the control module 220 could be connected directly to the control module 220 via electrical wires. A separate power unit, situated at a different location, could be used, for example, to deliver power to the stimulator 210 using power telemetry.

Typically, the apparatus 200 has to be calibrated. Calibration of the apparatus 200 can include calibrating the motion sensing system 222. The sensors of the motion sensing system 222 are calibrated to establish the relationship between the output signals of the sensors (for instance, rotation sensors such as the sensor 500 shown in FIG. 5) and the actual translation and rotational motion undergone by the person wearing the stimulator 200. Once that relationship is determined and represented as a mathematical mapping or transformation in the form of, for example, a matrix, the output signals (typically electrical voltage levels) sensed at the various sensing devices of the sensing system 222 are forwarded to the computing device 224 of the control module 220. There, the analog signals generated by the sensing devices are converted to digital signals using an analog-to-digital converter. Subsequently, the mathematical transformation or mapping determined during the calibration stage is applied to the digital signals to obtain a measure of the motion (rotational and/or translational) undergone by the person wearing the apparatus 200.

Calibration of the motion sensing system 222 can also include computation of mathematical transformations, represented by matrices, that convert the signals measured by the various sensing devices of the sensing system 222 so that the transformed motion signals are orthogonal to each other. The transformation can also be designed to translate the motion signals measured in one coordinate system to another coordinate system more suitable for generating the control signals provided to the optical stimulator 210.

Additionally, calibration of the apparatus 200 includes determining filtering to best provide the person's motion information. Parameters that correlate the person's motion, as predicted by the model, with the control feedback signals that are provided to the vestibular system are determined. As previously noted, the control feedback signals are encoded and transmitted to the optical stimulator 210, which then uses them to control its optical stimulation of the vestibular system. For example, if a high-pass filter is used to encode rotational information in a manner that mimics the normal dynamics of the canals and generates a control feedback signal needed to obtain rotational stability of a person's head, then the filter parameters would need to be determined. The determination of these parameters generally has to be performed concurrently with the determination of the level of optical illumination generated by the stimulator 210, as described below.

Calibration of the apparatus 200 also includes calibrating the level of optical illumination provided by the optical source 320 to each of the optical fibers 322*a-f*.

Calibration of the level of optical illumination by an optical source 320 is performed by examining the response of the person to various levels of stimulation given controlled movement and rotation of the person's body and/or head. For example, when the optical stimulator 210 is used to stimulate the vestibular system to provide control information to the central nervous system, the person may passively rotate or be asked to rotate his head towards a fixed pre-determined point in space. The level of optical illumination at each of the optical fibers 322*a-f* connected to the optical source 320, given the control feedback signal received from the computing device 224, is then manually varied until the point at which the level and/or manner of optical illumination by the optical fibers 322*a-f* enables the person to improve stability and balance (e.g., until the illumination level at which the person no longer experiences some of the clinical symptoms of instability, like dizziness), or until a desired response is obtained. For example, one way to calibrate the optical stimulator 210 is by monitoring the eye movements of the person in response to various levels of illumination. Since one of the functions of the central nervous system is to control the movement of the eye to enable clear vision during head motion, there is a strong correlation between stimulation of the vestibular system and movement of the eyes. Other ways to calibrate the stimulator 210 may also be used.

In operation, when the apparatus 200 is used to control the balance and stability of a person, sensing devices, such as the translation sensing device 400 and/or the rotation sensing device 500, mounted on the head of a person, sense rotational and translational motion of the head and/or body of the person. The sensing devices produce electrical signals that are sent to the computing device 224 of the control module 220. The computing device 224 processes the received signals to provide values or signals indicative of the motion undergone by the person. The processed signals are then used to produce control signals that are provided to the optical stimulator 210. The optical source 320 of the stimulator 210 generates optical illumination for each of the optical fibers 322*a-f* connected thereto. The transmitted optical illumination is the projected from the end of the respective optical fibers disposed proximate to various nerve areas, including nerve areas of the vestibular system.

When the apparatus 200 is used to produce jamming signals to counteract the non-stationary signals transmitted by the nerves of the vestibular system of a person suffering from Meniere's disease, the computing device 224 generates signals to modulate the generation of optical signals. The generated optical signals stimulate the nerves of the vestibular system (and/or other nerve areas) to cause them to generate nerve signals at a constant repetition rate. Generation of control signals by the computing device 224 can be triggered automatically when a sensing device senses the onset of an attack of Meniere's disease, or manually when the patient, or some other individual, operates a switch that causes the computing device 224 to generate and transmit the control signals to modulate the optical source 320.

Although FIG. 2 shows only a single stimulator 210, additional optical stimulators may be used. For example, a companion optical stimulator (not shown in the figure) may be placed in the person's other ear. Use of such an additional stimulator would be particularly useful to provide symmetric stimulation to alleviate bilateral vestibular conditions that affect a person's left and right vestibular organs (i.e., both ears). Further, use of multiple stimulators may also be desirable to more accurately mimic the complementary functioning of a person's bilateral (left and right side) peripheral vestibular organs. Further, the optical stimulator 210 may be used in conjunction with other types of stimulators and/or actuators. For example, the optical stimulator describe herein may be used with any of the mechanical actuators described in U.S. patent application Ser. No. 11/193,034, entitled "Mechanical Vestibular Stimulator", filed Jul. 29, 2005, the contents of which are hereby incorporated herein by reference in their entirety, and/or with the various stimulators (e.g., electrical, mechanical, or chemical) described in U.S. patent application Ser. No. 10/738,920.

Further, although FIG. 2 shows the apparatus 200 being used with a human being, the apparatus 200 can also be used with animals. The apparatus 200 need not be used only to alleviate medical conditions affecting a person's balance and stability, but can also be used for other conditions in which stimulation of the vestibular system is required or desirable. Further, the apparatus 200 may be used for non-therapeutic or even non-medical purposes. For example, the apparatus 200 can be used in the course of medical research to investigate the functioning of the brain.

Other Embodiments

A number of embodiments of the invention have been described. Nevertheless, it will be understood that various modifications may be made without departing from the spirit and scope of the invention. Accordingly, other embodiments are within the scope of the following claims.

What is claimed is:

1. A method for stimulating the vestibular system, the method comprising:

selecting a portion of a bony structure surrounding one or more nerve areas, the portion being sufficiently thin to allow light to propagate from a site external to the bony structure to the nerve areas, the nerve areas affecting a person's balance;

placing an end of an optical fiber at the site without breaching the bony structure;

directing light through the optical fiber to stimulate the nerve areas; and controlling generation of the light.

2. The method of claim 1, wherein controlling the generation of light comprises:

generating a control signal; and transmitting the control signal to an optical stimulator in optical communication with the optical fiber.

3. The method of claim 2, wherein generating the control signal comprises producing a jamming signal that causes the generation of stationary nerve signals transmitted to the brain.

4. The method of claim 3, wherein producing a jamming signal comprises:

detecting a non-stationary signal produced by the person's vestibular system; and producing the jamming signal in response to the detected non-stationary signal.

5. The method of claim 1 wherein directing light comprises directing laser light.

6. The method of claim 1, wherein controlling the generation of light comprises generating light in response to motion information indicative of the person's motion.

7. The method of claim 6, wherein generating light in response to motion information comprises:

detecting motion information; and processing the motion information.

* * * * *

UNITED STATES PATENT AND TRADEMARK OFFICE
CERTIFICATE OF CORRECTION

PATENT NO. : 7,488,341 B2 Page 1 of 1
APPLICATION NO. : 11/227969
DATED : February 10, 2009
INVENTOR(S) : Daniel Michael Merfeld

It is certified that error appears in the above-identified patent and that said Letters Patent is hereby corrected as shown below:

Title page, Item (54) Title and Col. 1, Line 1,
Please replace the title of the application with the following:

--OPTICAL VESTIBULAR STIMULATOR--

Signed and Sealed this

Twenty-fourth Day of March, 2009

JOHN DOLL
*Acting Director of the United States Patent and Trademark Office*

UNITED STATES PATENT AND TRADEMARK OFFICE
CERTIFICATE OF CORRECTION

| | | |
|---|---|---|
| PATENT NO. | : 7,488,341 B2 | Page 1 of 1 |
| APPLICATION NO. | : 11/227969 | |
| DATED | : February 10, 2009 | |
| INVENTOR(S) | : Daniel M. Merfeld | |

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by (443) days Delete the phrase "by 443 days" and insert -- by 592 days --

Signed and Sealed this

Twentieth Day of April, 2010

David J. Kappos
*Director of the United States Patent and Trademark Office*